United States Patent
Drews et al.

(10) Patent No.: US 7,336,191 B2
(45) Date of Patent: Feb. 26, 2008

(54) GAS-MEASURING SYSTEM

(75) Inventors: Ralf Drews, Lübeck (DE); Ingo Pooch, Ratekau (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 52 days.

(21) Appl. No.: 11/419,358

(22) Filed: May 19, 2006

(65) Prior Publication Data

US 2007/0063828 A1 Mar. 22, 2007

(30) Foreign Application Priority Data

Sep. 22, 2005 (DE) ............... 10 2005 045 272

(51) Int. Cl.
*G08B 17/10* (2006.01)
*F04B 49/00* (2006.01)

(52) U.S. Cl. .................... 340/632; 417/63
(58) Field of Classification Search .... 73/23.31–23.33, 73/23.36, 23.41; 417/63; 340/632, 633, 340/539.29, 539.1, 514, 539.11, 539.26, 539.22, 340/500, 505, 501

See application file for complete search history.

(56) References Cited

U.S. PATENT DOCUMENTS

| | | | | |
|---|---|---|---|---|
| 4,297,689 A | * | 10/1981 | Shaw et al. | 340/632 |
| 4,882,576 A | * | 11/1989 | Boyd | 340/632 |
| 5,596,314 A | * | 1/1997 | Goldstein | 340/632 |
| 5,774,038 A | * | 6/1998 | Welch et al. | 340/286.05 |
| 6,712,586 B2 | * | 3/2004 | Koyano et al. | 417/63 |

FOREIGN PATENT DOCUMENTS

DE 10140945 A1 3/2003

* cited by examiner

*Primary Examiner*—Benjamin C. Lee
*Assistant Examiner*—Jennifer Mehmood
(74) *Attorney, Agent, or Firm*—McGlew and Tuttle, P.C.

(57) ABSTRACT

A gas-measuring system is provided that is suitable for both mobile and stationary use. A mobile measuring device (2) with sensors (4, 5, 6, 7) for detecting gas concentrations and a base station (3) are provided for this purpose. The mobile measuring device (2) is inserted into a holder (31) of the base station (3) and the operating functions to the measuring device (2) are now switched over to the base station (3).

13 Claims, 2 Drawing Sheets

GAS-MEASURING SYSTEM

CROSS REFERENCE TO RELATED APPLICATIONS

This application claims the benefit of priority under 35 U.S.C. § 119 of German Patent Application DE 10 2005 045 272.8 filed Sep. 22, 2005, the entire contents of which are incorporated herein by reference.

FIELD OF THE INVENTION

The present invention pertains to a gas-measuring system with a mobile measuring device and a base station.

BACKGROUND OF THE INVENTION

A mobile gas-measuring device for the simultaneous detection of different pollution gases is known from DE 101 40 945 A1. Three electrochemical sensors, which are used to measure the concentrations of possible pollution gases in a gas sample, are located in a device housing. The gas concentration values measured by the sensors are processed by an evaluating unit integrated in the measuring device and outputted via a display unit. The evaluating unit checks the measured values for plausibility and for compliance with certain, preset limit values. An optical or acoustic alarm is triggered if limit values are possibly exceeded or in case of implausible measured values.

The prior-art gas-measuring device is carried by the user as a personal monitoring device, so that pollution gases are rapidly recognized in the work area. Due to the mobility of the gas-measuring device, which is normally attached directly to the clothing or the upper body, it must have the most compact housing dimensions possible and be lightweight. The capacity of the power supply unit carried by the user is limited as a result. In case of longer-lasting measurement, this has the consequence that gas measurements are performed at certain time intervals only to save power or that the sound level of alarm generators is limited.

In case of a gas-measuring device, which is arranged stationarily in the environment of a user and continuously monitors the pollution gas content in the ambient atmosphere, it is required that the power supply should make possible a long use time and that possible warning messages be communicated to the user in a clearly perceptible manner, especially in case of high background noise level. Such gas-measuring devices can be carried by the user only to a limited extent.

Consequently, two different monitoring systems are normally needed, namely, a personal monitoring device, which is carried by the user, and a stationary monitoring device, which is arranged in the work area of persons. Different measuring systems must usually be kept ready for this purpose, which increases the costs, especially due to the fact that twice the number of gas-measuring systems must be kept ready.

SUMMARY OF THE INVENTION

The basic object of the present invention is to provide a gas-measuring system that is suitable for both mobile and stationary use.

According to the invention, a gas-measuring system is provided with a mobile measuring device, which comprises sensors for detecting gas concentrations and a first control and calculating unit for processing the measured signals sent by the sensors and means for data transmission. A base station is provided having a holder for receiving the measuring device, a power supply unit, a second control and calculating unit for actuating the alarm generators arranged in the base station and interfaces for supplying gas to be measured to the sensors and for data exchange between the mobile measuring device and the base station.

The advantage of the present invention is essentially that a base station for accommodating a mobile measuring device is designed such that the gas sampling takes place via the base station and warnings and alarms are communicated to the user from the base station via corresponding optical and acoustic transducers. Interfaces, which send the sample gas flow to the sensors, on the one hand, and couple the mobile measuring device to the base station for the transmission of data, on the other hand, are provided for this purpose between the mobile measuring device and the base station. The base station has a separate control and calculating unit, so that bidirectional data exchange is possible between the measuring device and the base station and the user can determine individually which functions are performed via the measuring device and what support is needed from the base station. The display fields and the alarm generators can be dimensioned larger at the base station, because the space available for installation is not limited here. This facilitates the reading of measured values and acoustic warnings can be communicated to the user in a more clearly audible manner. The user can also decide whether he performs the operation of the measuring device from the base station or whether certain settings take place directly at the mobile measuring device. Provisions are preferably made for the operating functions to be switched over automatically from the measuring device to the base station when the mobile measuring device is placed into the holder of the base station.

The base station is designed such that gas sampling can also be carried out from a remotely located measuring point. A gas sampling tube is connected for this purpose to a measured gas pump arranged in the base station. The housing of the base station has a cable drum-like design, so that a long measuring gas tube can also be carried with the base station. High stability is obtained due to the base station designed in the form of a cable, because a side surface of the cable drum can be used as a base. The opposite side surface is used to receive the mobile measuring device. The side surfaces of the base station are advantageously of an annular design, so that the ring can also be used as a grip surface for transporting the base station.

The base station advantageously has additionally an interface for transmitting electricity to the mobile measuring device. The use time of the mobile measuring device is thus prolonged, because the capacity of the power supply unit of the base station can be fully exhausted.

An exemplary embodiment of the present invention is shown in the drawings and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
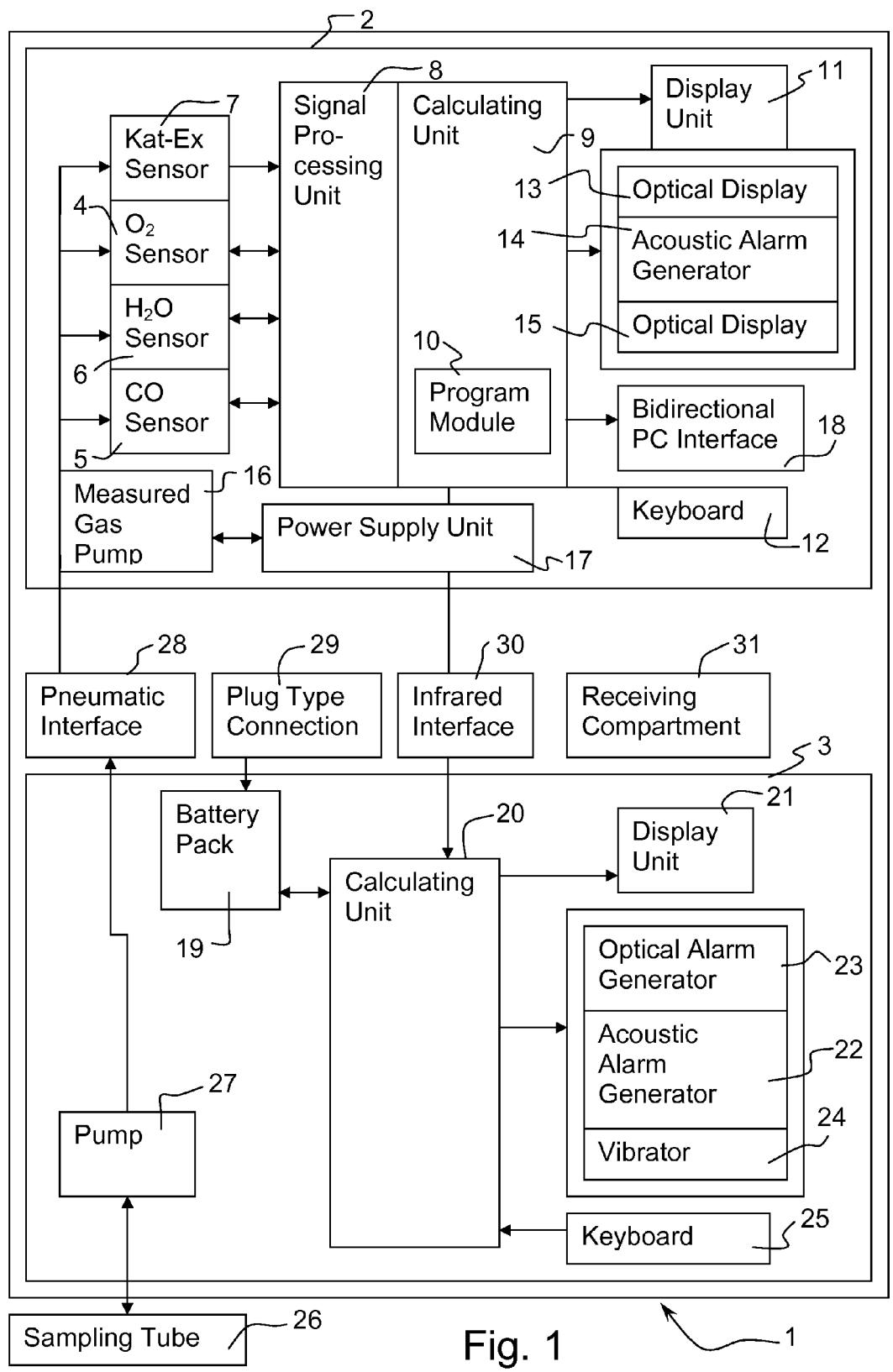
FIG. 1 is a gas-measuring system with a mobile measuring device and a base station according to the invention.

Referring to the drawings, in particular FIG. 1, schematically illustrates a gas-measuring system 1, which comprises a mobile measuring device 2 and a base station 3. The mobile measuring device contains an oxygen sensor 4, a CO sensor 5, an $H_2S$ sensor 6 and a Kat-Ex sensor 7 that determines the concentration of combustible gases by catalytic combustion. The sensors 4, 5, 6, 7 are connected via a signal processing unit 8 to a first central control and calculating unit 9, which evaluates the measured gas concentrations by means of a program module 10 and outputs them via a display unit 11. Warning limits can be assigned to the individual measured gas concentration values via a keyboard 12. Possible alarms are sent via an optical display 13, an acoustic alarm generator 14 or via a vibrator 15. A measured gas pump 16 delivers the gas sample to be analyzed to the sensors 4, 5, 6, 7. A power supply unit 17 supplies the measuring device 2 with electricity. Measured and status data can be read via a bidirectional PC interface 18. Program updates can also be read into the program module 10 with the PC interface.

The base station 3 contains a battery pack 19, a second control and calculating unit 20, a display unit 21, an acoustic alarm generator 22, an optical alarm generator 23 and a vibrator 24. A keyboard 25 is used to enter data of warning limits, which are assigned, e.g., to the gas species. The gas sampling is carried out via a sampling tube 26 and a pump 27.

The mobile measuring device 2 and the base station 3 are connected to one another via a pneumatic interface 28, a plug type connection 29, an infrared interface 30 and a receiving compartment 31.

The pneumatic interface 28 is used to pass on the gas sample drawn in by the pump 27 via the measured gas pump 16 to the sensors 4, 5, 6, 7. The plug type connection 29 couples the battery pack 19 with the power supply unit 17, so that the capacity of both power supply units 17, 19 can be utilized. Bidirectional data connection is established via the infrared interface 30 between the control and calculating units 9, 20. The mobile measuring device 2 is inserted into the receiving compartment 31 for operation and locked. The pneumatic and electric connections may then be established via the interfaces 28, 29, 30.

When the mobile measuring device 2 is inserted into the receiving compartment 31, the control and calculating unit 9 transmits a device code to the control and calculating unit 20 of the base station 3. A comparison is performed there with stored, permissible codes, and a release signal is generated for the bidirectional data exchange. The display unit 11, the alarm generators 13, 14, 15 and the keyboard 12 are deactivated in another step and the display unit 21, the alarm generators 22, 23, 24 and the keyboard 25 of the base station 3 are connected to the mobile measuring device 2 via the infrared interface 30 for data exchange. The mobile measuring device 2 is operated exclusively from the base station 3.

However, the program module 10 in the mobile measuring device is designed such that partial functions can also be transferred from the mobile measuring device to the base station 3. Corresponding inputs can be made and values can be preset from the keyboards 12, 25.

Figure 2:
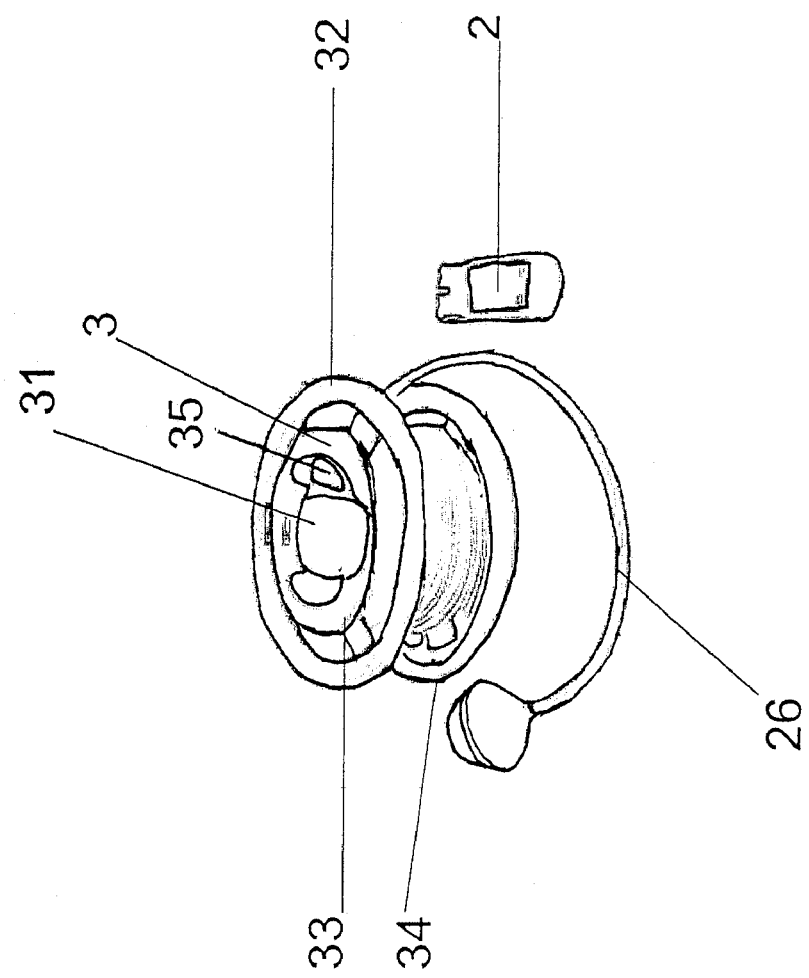
FIG. 2 is a perspective view of the mobile measuring device and the base station.

FIG. 2 shows a perspective view of the mobile measuring device 2 and the base station 3. Identical components are designated by the same reference numbers as in FIG. 1. The housing of the base station has a design similar to that of a cable drum with an upper ring 32, a middle part 33 and a lower ring 34. The base station 3 is placed on the lower ring 34 during measuring operation and the measured gas tube 26 for gas sampling can be unwound from the middle part 33. Due to the cable drum-like design of the base station, it is also possible to accommodate longer measured gas tubes 26 on the base station 3 without handling being compromised by this in any way. Depending on the particular application, a certain length of the measured gas tube 26 can be unwound from the base station 3. The alarm generators 22, 23, 24, which are not shown in greater detail, the keyboard 25 and the display unit 21 are arranged in a control panel 35 on the upper ring 32 of the base station 3.

While specific embodiments of the invention have been shown and described in detail to illustrate the application of the principles of the invention, it will be understood that the invention may be embodied otherwise without departing from such principles.

What is claimed is:

1. A gas-measuring system comprising:
   a mobile measuring device comprising sensors for detecting gas concentrations, a first control and calculating unit for processing measured signals sent by said sensors and transmission means for data transmission;
   a base station having a holder for receiving said measuring device, a power supply unit, alarm generators arranged in said base station, a second control and calculating unit for actuating said alarm generators and interfaces for supplying gas to be measured to said sensors and for data exchange between said mobile measuring device and said base station.

2. A gas-measuring system in accordance with claim 1, wherein said base station is provided with a measured gas pump for sampling gas.

3. A gas-measuring system in accordance with claim 2, wherein a sampling tube is connected to said measured gas pump and that said base station has a cable drum-like mount for said sampling tube.

4. A gas-measuring system in accordance with claim 3, wherein an upper ring of said base station receives said holder for said mobile measuring device and a lower ring is designed as a base.

5. A gas-measuring system in accordance with claim 1, wherein said base station is designed such that when said measuring device is inserted into said holder, said alarm generators are switched to a functional connection to said first control and calculating unit.

6. A gas-measuring system in accordance with claim 1, wherein said base station further includes an interface for transmitting electricity to said measuring device.

7. A gas-measuring system comprising:
   a mobile measuring device comprising a sensor for detecting a concentration of a gas, a mobile device control and calculating unit for processing measured signals sent by said sensor and a transmission device for data transmission;
   a base station having a base station body, a holder for receiving and supporting said measuring device, a power supply unit, alarm generators connected to said base station body, a base station control and calculating unit for actuating said alarm generators, an interface for supplying gas to be measured to said sensor and an interface for data exchange between said mobile measuring device and said base station.

8. A gas-measuring system in accordance with claim 7, wherein said base station is provided with a measured gas pump for sampling gas.

9. A gas-measuring system in accordance with claim 8, wherein a sampling tube is connected to said measured gas pump.

10. A gas-measuring system in accordance with claim 7, wherein said base station body includes a spool structure with a central support part and a mount for said sampling tube.

11. A gas-measuring system in accordance with claim 10, wherein said base station body includes an upper ring connected to said central support part that defines a support to receive a holder for said mobile measuring device and a lower ring forming a base.

12. A gas-measuring system in accordance with claim 7, further comprising switching means for switching said alarm generators to a functional connection to said mobile measuring device control and calculating unit upon said measuring device being inserted into said holder.

13. A gas-measuring system in accordance with claim 7, wherein said base station further includes an interface for transmitting electricity to said measuring device.

* * * * *